United States Patent [19]

Kwee et al.

[11] Patent Number: 5,060,250
[45] Date of Patent: Oct. 22, 1991

[54] METHOD AND SYSTEM FOR DETECTING DEFECTS IN TIRE SIDEWALLS

[75] Inventors: Henry T. Kwee; Alexandra Valsamidis, both of Akron, Ohio

[73] Assignee: The Goodyear Tire & Rubber Company, Akron, Ohio

[21] Appl. No.: 488,828

[22] Filed: Mar. 6, 1990

[51] Int. Cl.⁵ .................... G01B 15/06; G01N 23/02
[52] U.S. Cl. ........................... 378/61; 378/58; 378/10
[58] Field of Search ..................... 378/61, 58, 10

[56] References Cited

U.S. PATENT DOCUMENTS 4,706,267  11/1987  Chase et al. ................ 378/58
4,949,366  8/1990  Collmann ..................... 378/61

FOREIGN PATENT DOCUMENTS 0239689  10/1987  European Pat. Off. .

Primary Examiner—Edward P. Westin
Assistant Examiner—Don Wong
Attorney, Agent, or Firm—David E. Wheeler; R. J. Slattery, III

[57] ABSTRACT

A positioning arm (44) is provided with a plurality of elongated members carrying two combinations of a radiation source (46; 58) and a sensor (48; 60). Each sidewall is interposed between a radiation source (46; 58) and a sensor (48; 60). The radiation sources (46; 58) provide a collimated beam of radiation which is relatively unattenuated (absorbed) in passing through the elastomer in the tire sidewall, but will be reflected by the steel wire cords in the sidewall. Each combination of a radiation source and sensor scans a sidewall of the tire at a predetermined speed to detect sidewall defects such as missing or improperly spaced cords.

15 Claims, 8 Drawing Sheets

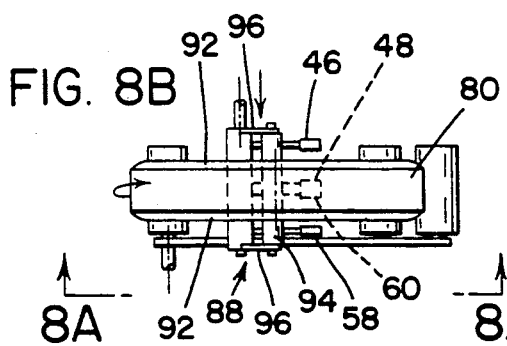
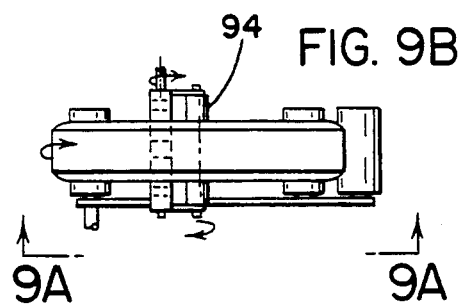
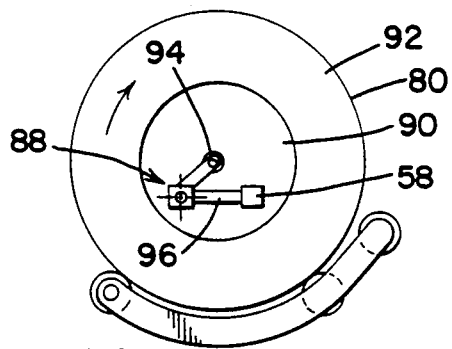
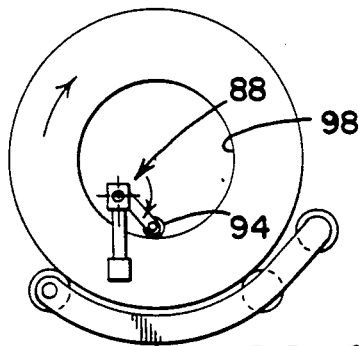
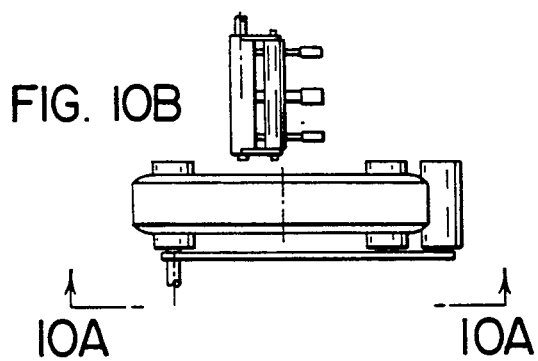
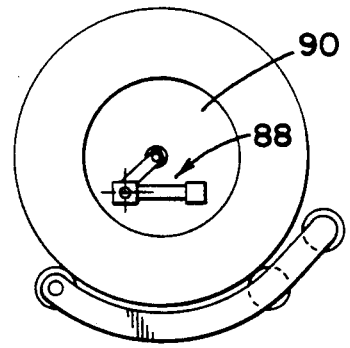
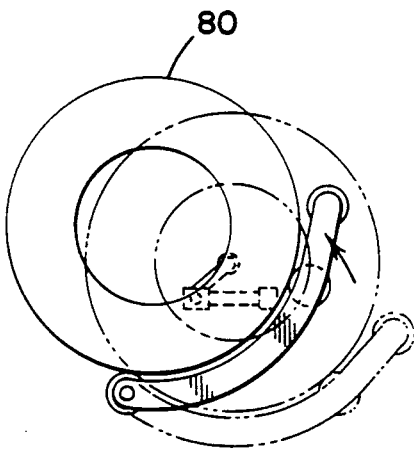

METHOD AND SYSTEM FOR DETECTING DEFECTS IN TIRE SIDEWALLS

BACKGROUND OF THE INVENTION

This invention relates generally to the detection of defects in cured and uncured tires. More specifically this invention relates to the detection of defects in the sidewalls, such as for example: missing wires, uneven spacing between adjacent wires, and variances in the gauge of the tire sidewall.

Various methods and systems have been used to inspect various parts of tires, such as for example ultrasonics, microwaves, X-rays, etc. Most systems however have not lent themselves to be used in production settings because of one or more various problems. These have included too slow of a cycle time, the cost of the equipment, and the accuracy of the results. As a result 100% testing of tires has not been practiced and has resulted in a sampling approach relating to the tires produced.

It still is however, desirous in the industry to provide a means for testing tires in a production line where virtually all tires are tested. The sidewall area of a tire is one such area where it is desirous to inspect all the tires in a production line.

In one embodiment, the present invention relates to a system for inspecting tire sidewalls by detecting missing or overlapping cords within an elastomer of the sidewalls of a tire, the system comprising: (a) a radiation source or sources for providing a collimated beam of radiation through each tire sidewall, the radiation being less attenuated or reflected by the elastomer of said sidewalls than by the cords: (b) a sensor or sensors aligned in combination with each radiation source, each sensor or sensors detecting the collimated radiation and generating an electrical signal in response to the radiation: (c) a positioning arm, the radiation source or sources and the sensor or sensors being attached to the positioning arm: (d) a positioning means for causing said positioning arm to interpose a tire sidewall between each radiation source and sensor; (e) a means for causing each radiation source and sensor to scan along a section of the tire sidewall at a predetermined speed; (f) means responsive to the electrical signal generated by each sensor for providing a timing signal when each said sensor bears a predetermined relationship to each scanned cord in the tire sidewall; and (g) means responsive to said timing signal associated with each sensor during a predetermined scan for mesasuring the time each scanned cord is between a radiation source and a sensor.

Also provided is a method of detecting defects in tire sidewalls, the method comprising the steps of: (a) interposing a tire sidewall between a radiation source or sources and a sensor or sensors: (b) passing a collimated beam of radiation from a radiation source or sources through a tire sidewall, such radiation being less attenuated or reflected by the elastomer of the sidewall than the scanned cords: (c) detecting radiation passing through a tire sidewall by a sensor or sensors; (d) causing each radiation source and sensor to scan along a section of tire sidewall at a predetermined speed: (e) providing a timing signal, responsive to an electrical signal received by a sensor when a sensor bears a predetermined relationship to each scanned cord in the tire sidewall: (f) measuring the time each scanned cord is between a radiation source and a sensor, responsive to the respective timing signal generated.

BRIEF DESCRIPTION OF THE DRAWINGS

The following is a brief description of the drawings in which like parts bear like reference numerals and in which:

FIGS. 7A through 10A are plan views of the steps according to Example 1;

FIGS. 7B through 10B are elevational views taken along the respective A-A line of the plan views of Example 1:

FIG. 11 is an elevational view of a step of Example 1:

DESCRIPTION OF THE INVENTION

Figure 1:
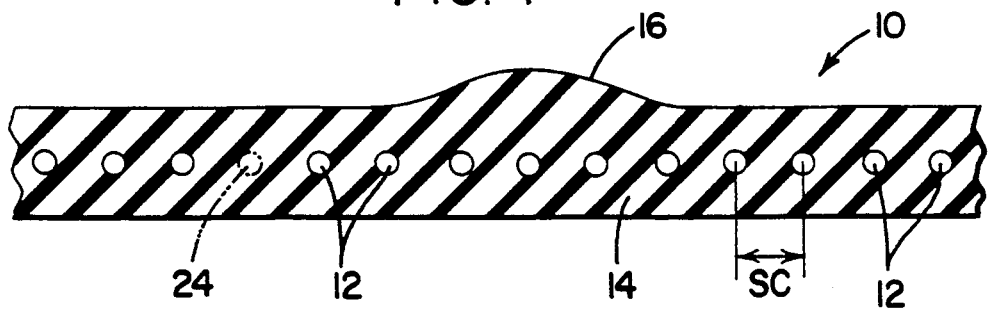
FIGS. 1-3 are cross sectional views of a tire sidewall illustrating various abnormalities associated with the carcass cords.
Figure 2:
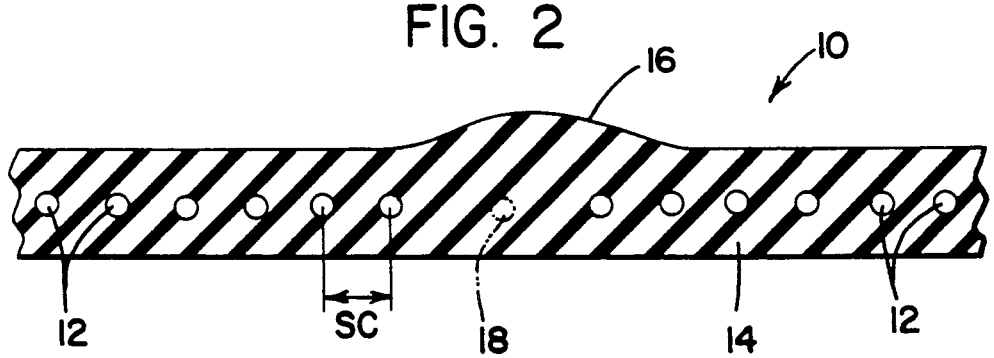
Figure 3:
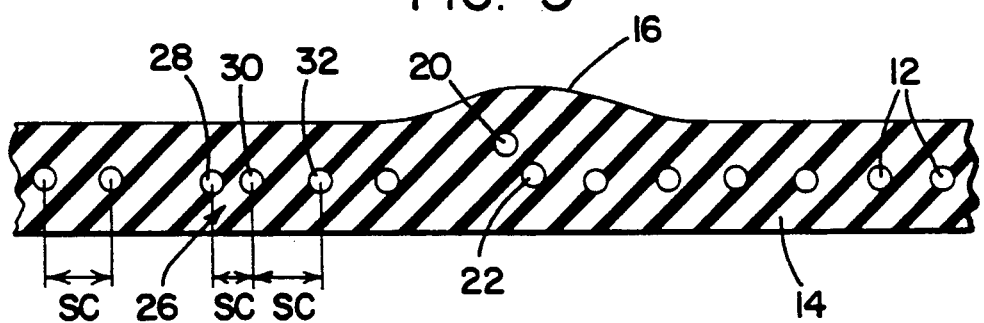

With reference to FIGS. 1, 2, and 3, there is illustrated a cross-sectional view of a tire sidewall, shown generally as reference numeral 10. The tire sidewall 10 comprises a plurality of carcass cords or wires 12 which are embedded within an elastomer 14. Uneven distribution of the elastomer 14 may produce a bulge 16 in the tire sidewall. This bulge 16 may indicate only an excess of elastomer such as in FIG. 1 or it may indicate that a cord 18, FIG. 2, is missing, or it may indicate a twisting of cords 20, 22, FIG. 3. The former may only detract from the appearance of the tire while that later two may adversely effect the life of the tire. It therefore is important to be able to determine the cause of a bulge in a sidewall.

Tire sidewalls can also have undesirable wire spacings which may or may not be readily apparent to the naked eye. For example, while the missing cord 18 resulted in a bulge in FIG. 2 in some cases a missing cord 24, FIG. 1, does not produce a corresponding bulge. Furthermore, the spacing between cords (SC), while generally uniform, may vary, shown generally as reference numerals 26, FIG. 3, if the cords 28, 30 and 32 become shifted during the process of manufacturing the tire. These conditions may also prove to have an adverse effect upon the life of a tire.

Figure 4:
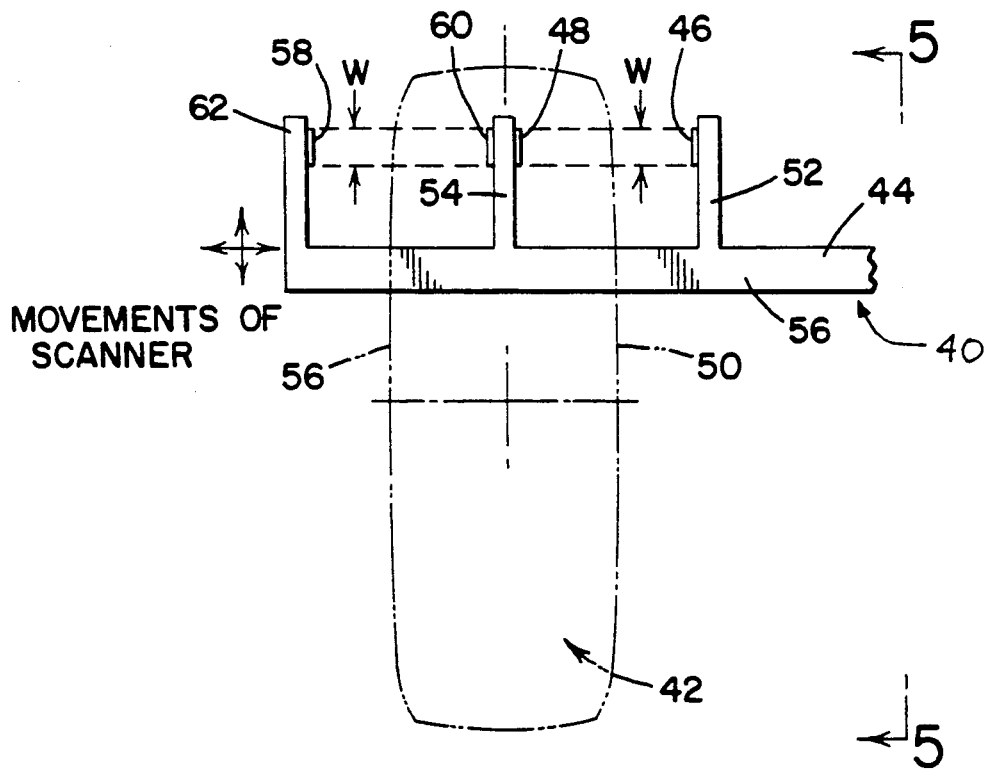
FIG. 4 is a partial elevational view according to one aspect of the invention showing a means for scanning the sidewalls of a tire.
Figure 5:
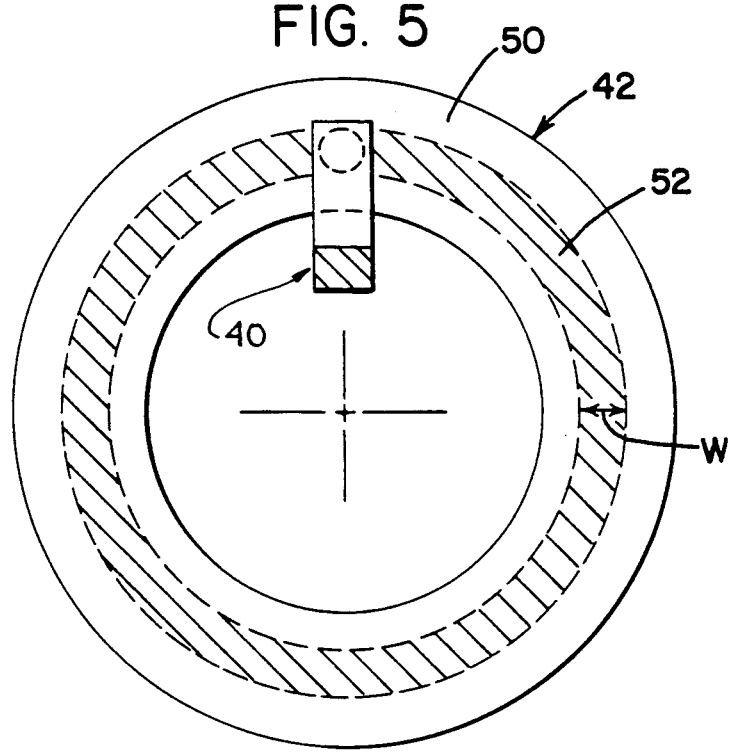
FIG. 5 is an elevational view taken along line 5-5 of FIG. 4.

With reference to FIGS. 4 and 5 there is illustrated a means shown generally as reference numeral 40 for scanning the sidewalls of a tire 42. The means comprises a positioning arm 44 having a first radiation source 46 and a first sensor 48 attached to the positioning arm. The first radiation source 46 provides a highly collimated X-ray beam of radiation through the tire sidewall 50. A greater amount of the radiation will penetrate the elastomer of the sidewall than through the steel carcass cords. The sensor 48 is aligned with the collimated beam of radiation from the radiation source 46 for detecting the radiation passing through the tire sidewall 50.

The combination formed by radiation source 46 sensor 48 is scanned along a section 52 of the tire sidewall, having a width W.

Over the entire circumferential length of the section 52 there must be not only a certain minimum amount of cords, but they must be properly spaced. The section 52 may then be divided circumferentially into a plurality of small portions or windows. Each window therefore, must contain a minimum number of cords within this arc length and they must be properly spaced. The arc of a window is believed to be preferred to be an angular displacement as determined from a radius extending from the axis of rotation of the tire. For example each window may have a 10° arc length. This may cause the circumferential distance of the arc length to vary from one tire size to the next.

Radiation transmitted to the sidewall 50 from the radiation source 46, will be relatively unattenuated (absorbed) in passing through the elastomer in the tire sidewall, but will be reflected by the steel cords in the sidewall. The sensor 48 then, will receive varying amounts of radiation as the cords and the elastomer between the cords are scanned.

The combination of source 46 and sensor 48 may be attached to elongated members or arms 52, 54, respectively, extending from a main elongated member 56, to form substantially a "U" in an elevational view. While the combination or pair of radiation source 46/sensor 48 can be used to scan one tire sidewall and then moved to scan the other tire sidewall 56, this would take twice as long as if both sidewalls were scanned at the same time. Therefore in the preferred embodiment both tire sidewalls 50, 56 are scanned simultaneously. This can be accomplished by the use of a second combination of a radiation source 58 and sensor 60, similar to the first combination of source and sensor. The second combination is also attached to the positioning arm 44. Another elongated member or arm 62 is attached to the main arm 56 and carries the second radiation source 58 while the second sensor 60 is attached to the arm 54 to which the first sensor 48 also is attached, to form substantially an additional "U" in the elevational view of FIG. 4.

In this manner radiation is transmitted from the exterior of the tire through the tire sidewalls 50, 56 where it is received by the sensors 48, 60, respectively. Alternatively the position of the sensors and radiation sources could be reversed such that the radiation sources are carried by the arm 54 to transmit outwardly through the sidewalls to the sensors. This approach could be substituted in the examples set forth below. The former approach however is preferred over the latter.

Figure 6:
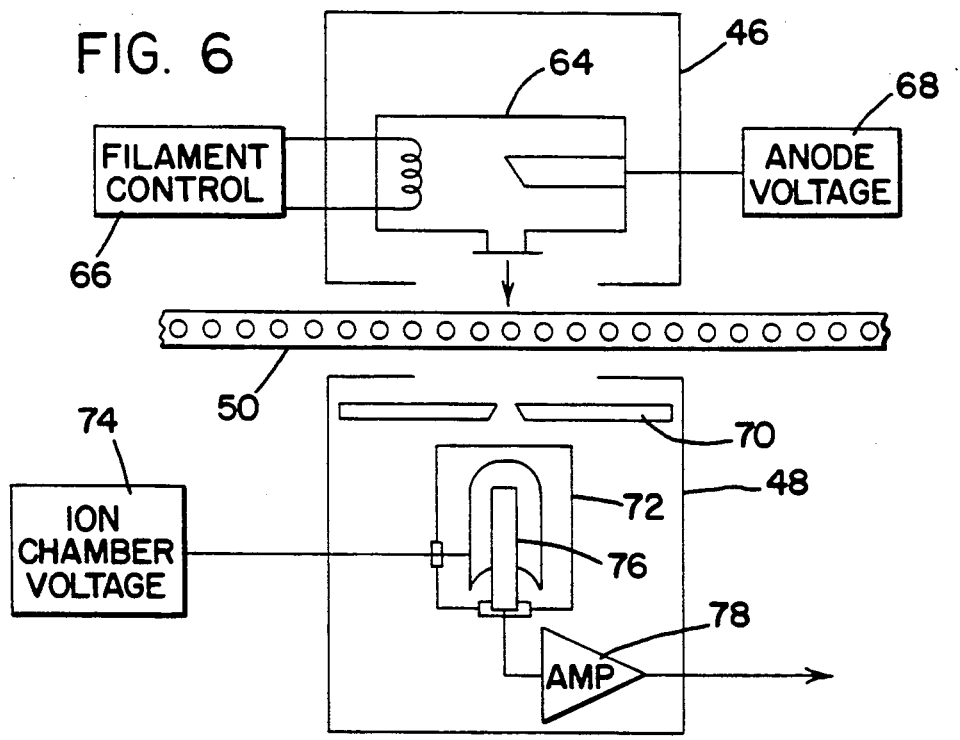
FIG. 6 is a schematic diagram of the source and sensor for use in the present invention according to one aspect thereof.
Figure 7B:
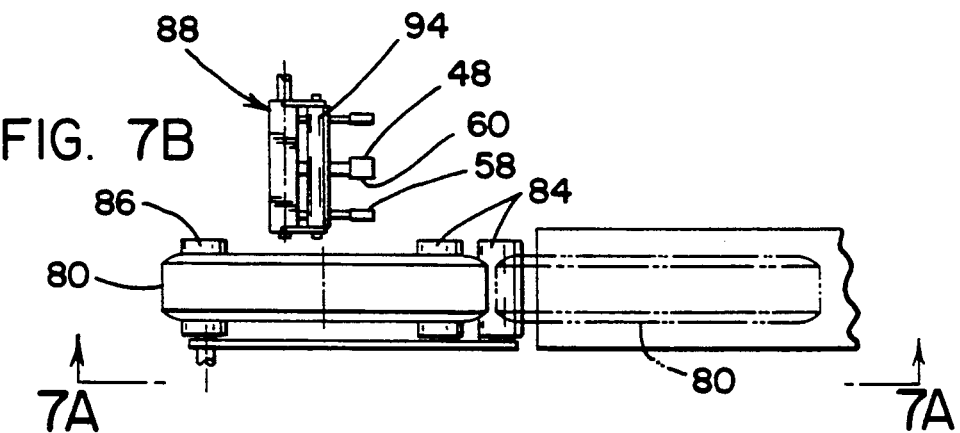
Figure 7A:
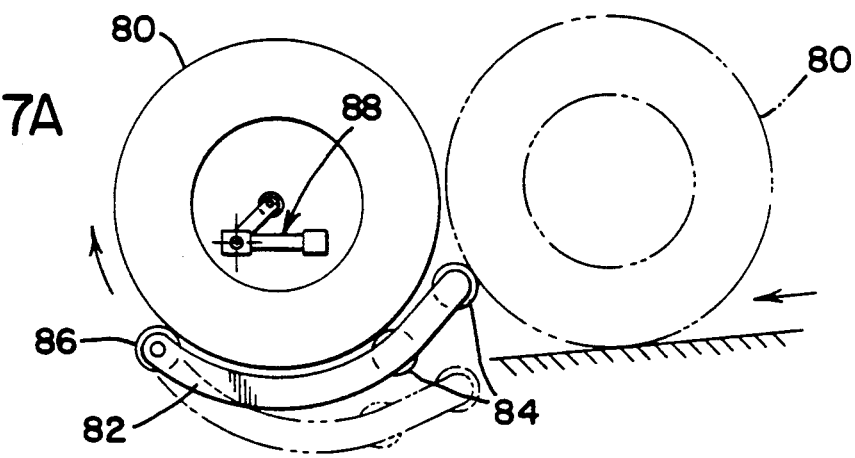

With reference to FIG. 6 the radiation source 46 comprises an X-ray tube 64, energized by a filament control 66 and anode voltage source 68, to emit a relatively narrow X-ray beam through the tire sidewall 50 and through an aperture slit 70 of the sensor 48 into ionization chamber 72. The aperture slit provides a narrow beam width and good definition of the edges of the cords. Alternatively, the beam emitted by source 46 could be collimated before it passes through the tire sidewall. Ionization within chamber 72 permits a current to flow from the ionization chamber voltage source 74 to central electrode 76. The operation of ionization chamber detectors for the detection of X-rays is well known so that it is not believed necessary to explain the operation of this portion of the invention in more detail.

It is sufficient to note that when one of the steel cords of tire sidewall blocks the X-ray beam, the output of amplifier 78 is low, but when only the elastomer is between the X-ray tube and the ionization chamber the amplifier output is high.

Each source 46, 58 and sensor 48, 60 combination scans the respective sidewall at a constant speed detecting the presence or absence of cords. Clock pulses occurring at a relatively high rate are gated to a counter during the time the X-ray source is encountering a steel cord. The total count gated for each window of the sidewall represents the time portion of each window during which cords were present in the collimated x-ray beam, and thus is a measure (scaled by the clock rate) of the number of cords in each window. In that this method results in many counts per cord, a fractional cord within the window can be accounted for while a missing cord will be evidenced by a substantial decrease in the count of clock pulses. Pulses are generated during the scan to indicate the start of each window by a start of window pulse generator coupled to the source and sensor.

The processing of the signals produced by the sensors in relationship to the radiation received by them is described in further detail in U.S. Pat. No. 4,706,267 to Chase et. al, the entire disclosure of which is hereby incorporated herein by reference, especially the disclosure beginning on col. 3 line 2 and ending at col. 5 line 26. The reference to a "slice" in 4,706,267 is substantially equivalent to a "window" as used herein.

The inventive system should be able to accommodate a number of different tire sizes and types such that several different tire lines could be inspected by one machine. This may result in the number of cords per window varying from one tire to the next. It therefore is preferred that the machine can automatically determine or know the number of cords and/or counts for a window of a given tire. One way is to determine the number of cords or counts per window for several consecutive windows and take the average to determine the reference value to be used or compared with the counts obtained by subsequent windows. For example the first ten windows could be used to determine the average value of the count to be compared with subsequent windows as described above. With use of the reference value determined in this manner, a threshold can be determined, such that any count for any given window which is a certain number or percentage less or over the reference value could then trigger an alarm condition. This will necessitate scanning again the portion (the windows) of the tire used to provide the reference value to determine if in fact there are any missing cords in this area.

It is preferred that the threshold value determined above, will at the least, indicate when the wire to wire spacing, as measured from the center of one cord to the center of the next adjacent cord at some radius, is about two times the average spacing between cords of the windows used to provide the reference value above. In other words the system should be able to determine that a wire is either missing or has crossed itself with another wire.

Other methods of averaging could be employed to determine the reference value. For example the average over the entire circumference of the tire could be determined for one revolution and this number compared with the values determined for each window during the next tire revolution.

Ideally the detection should also be able to determine not only if the wires are crossed or missing but also if the spacing is not uniform between the wires. A wire may be displaced sufficiently from its intended spacing that although it is not crossed or missing the result may affect the life of the tire.

Figure 13:
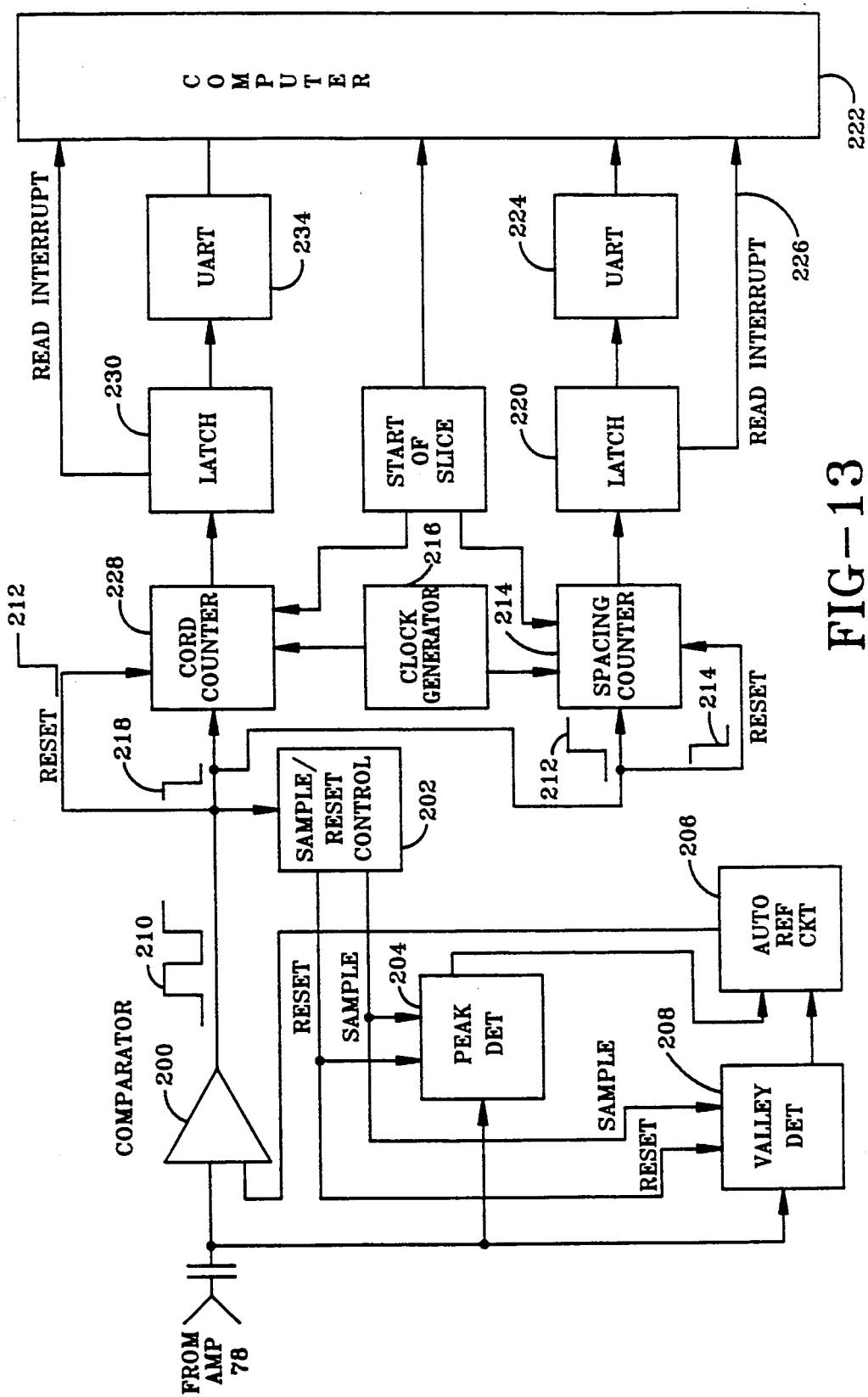
FIG. 13 is a block diagram of the electronics portion of one embodiment according to this invention.

This can be accomplished by providing a timing signal which is responsive to the electrical signal received by the sensors when the sensor is between cords For example refer to FIG. 13, wherein the block diagram of the electronic portion of U.S. Pat. No. 4,706,267 has been modified.

In this example the signal from the amplifier 78 of FIG. 6 is fed into a comparator 200 having a feedback loop of a sample/reset control 202, a peak detector 204, auto reference circuit 206 and a valley detector 208 to produce a shaped signal 210 as described in U.S. Pat. No. 4,706,267.

Figure 14:
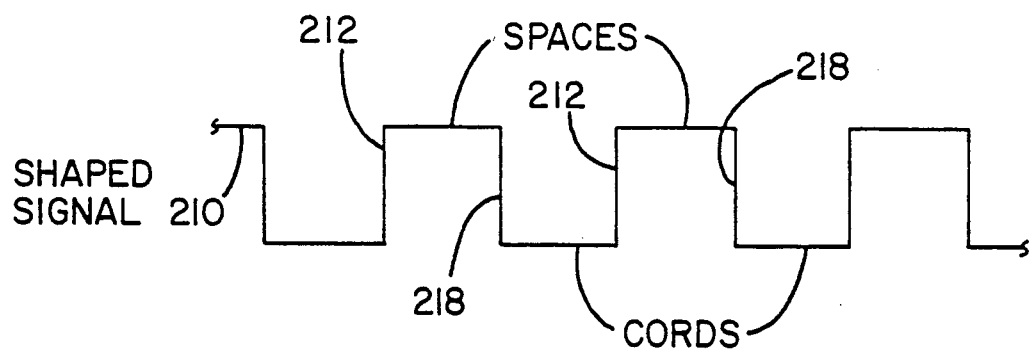
FIGS. 14 and 15 shows a wave form generated during scanning and the associated clock pulses.
Figure 15:

With reference to FIGS. 13, 14 and 15 the occurrence of a positive-going signal transition 212 causes the spacing counter 214 to count pulses 215 from, a clock generator 216 or from its own internal oscillator, so long as the output of the comparator is positive. The occurrence of a negative going transition 218 of the shaped signal causes the counter 214 to stop counting, transfer the count of the spacing counter 214 into a latch 220 and then reset the counter 214 to zero to await the next pre-going transition. The spacing counter will begin counting again with the occurrence of the next positive going transition of the shaped signal.

The count of the spacing counter 214 latched into latch 220 is then transferred to the computer 222 by various means known well in the art, one of which is by the use of an interface 224, such as a UART and a read interrupt signal shown as line 226.

The count received by the computer, representing the count from the spacing counter, could then be stored for each wire spacing to be used in further processing. However, it is believed that the spacing count received by the computer could be compared with the previous spacing count received and the larger of the two would be stored. The first spacing count received by the computer in a window or slice would always be stored because the storage would be reset to zero with each start of slice pulse. The second spacing count received would then be compared to the count held in storage with the largest count being retained. At the end of a window or slice the computer could therefore compare the largest number held in storage to a reference number indicating the average spacing, and if this number exceeded by a certain percentage, such as 150%, 175%, etc. an alarm could be indicated. Therefore, it would be known that there was a spacing error within the respective window or slice. Alternatively the spacing count of each interval the wires could be compared to the reference number indicating the average spacing. In this manner all the spacings would be compared and an alarm given at that location or time.

It is preferred that the clock generator, or the internal oscillator of the spacing counter, is set to produce pulses 215 at a rate which will be high with respect to the time of travel between cords. This is to assure a more accurate count.

Also, instead of counting the intervals between the wires to obtain the spacing information, the spacing counter 218 could be arranged to count from the beginning of a positive shaped signal transition to the beginning of the next positive shaped signal transition. This would result in counting not only the space between wires but also one wire itself. This would allow for the determination of the wire to wire spacing based upon the distance from centerline to centerline of the wires, in that the diameter of the wires are constant. Even if the wire diameters varied, the spacing could be calculated from continued subtraction of the cord counter data from the counts obtained between positive-going edges. The largest spacing count within a window or each spacing count could then be compared to a reference value and an alarm condition actuated upon exceeding it by a certain amount as described above.

Furthermore, if a minimum spacing between wires is not to be exceeded this could be accomplished by comparing the spacing between wires and signaling an alarm when the count did not reach a certain minimum value.

The remainder of the circuit could include cord counter 228 and latch 230 wherein the cord counter 228 would begin counting when the shaped signal 210 had a negative-going transition 218 and would continue until the next positive-going transition 212. The counter would count pulses either generated by an internal oscillator or more preferably from the clock generator 216. The cord counter could continue to count during the negative portions of the shaped wave 210 until the next start of slice pulse wherein the total count would be transferred to the latch 230 and then through the interface or UART 234 to the computer 222 similar to that described in U.S. Pat. No. 4,706,267. However it is preferred to allow the cord counter to count the pulses of each negative portion (corresponding to a wire) and then transfer this count to the computer 222. In this manner the computer would received each wire count in a slice or window and could perform the summation of cord counts per window or slice internally and then compare this to the reference cord value as described above.

Furthermore, receiving the individual cord counts would further help in automatically determining reference values for comparison. For example, the average number of counts per cord could be determined for several windows. This number could then be multiplied by a constant and the result subtracted from the average count of the cords per slice to determine a threshold that must be exceeded. If the average count per cord was determined to be 100 counts and the average number of counts per slice or window was determined to be 1000, the threshold count that each slice would have to exceed would then be $1000-(100 \times N)$ where N is a constant of 1 or less. To look for a missing wire only, N would be equal to 1. To look for a missing wire and/or crossed wires N would be less than 1, for example 0.7. Therefore if N is equal to 0.7 then if the count did not exceed 930 (1000−70) there would be an indication that there was at least a missing or crossed wire.

Each source/sensor combination can be caused to scan the tire sidewalls by a number of different means or methods: firstly the tire can remain stationary while the positioning means or arm is rotated: secondly, the positioning arm can be held stationary while the tire is rotated; and finally both can be moved or rotated at the same time. It is preferred that the tire be rotated while the positioning arm is stationary.

While both cured and uncured tires can be inspected, it is preferred to inspect cured tires after they leave the press area.

EXAMPLE 1

With reference now to FIGS. 7-11, a tire is transported to an inspection stand which it enters vertically. In other words, it is preferred that the tire 80 will roll into the inspection stand and remain in the vertical position, FIG. 7A. The inspection stand is provided with a means for holding the tire while also allowing it to be rotated, such as a well 82 having rollers 84. One of the rollers 86 is driven to provide for the rotation of the tire. The inspection stand may further be provided with two idler roll arms (not shown), placed at the top of the stand to keep the tire from bouncing, and two side rollers (also not shown), one for each side of the tire to keep the tires from deviating from the vertical position while it is being rotated.

Once the tire 80 is in position within the well of the inspection stand, the tire will begin to rotate via direct contact with the driving roller 86. The detection unit, indicated generally by reference numeral 88, FIG. 7B, remains in the retracted position until the tire is rotating at a constant predetermined speed, such as for example 12 rpm, (one revolution per five seconds) and in a stable manner, i.e., with a minimum amount of bouncing and/or movement of its rotational axis.

Once the above conditions have been met, the detection unit 88 moves through the bead opening 90, FIGS. 8A and 8B, such that each combination of radiation source 46, 58 and sensor 48, 60 is interposed between a sidewall 92 of the tire 80.

The detection unit 88, having been provided with an idler roller 94, attached to the elongated member 44 by a pair of arms 96, is rotated, FIGS. 9A and 9B, until the idler roller 94 engages the inner portion of the beads 98. This should position the radiation source/sensor combination to scan the desired portion of the tire sidewall. In the above example the detector is rotated about 90° to place it in the vertical position. Once into position the tire sidewalls are scanned.

Once removed, the rotation of the tire is stopped and the well 82 ejects the tire.

EXAMPLE 2

FIGS. 12A-G are referenced to this example.

As an alternate method, a tire can be transported to the inspection area where it can be inspected in the horizontal position. For example, a tire 100 is transported along a roller conveyor 102 until it reaches a section having rollers 104 to provide an opening 106 in the conveyor which corresponds to the bead opening 108 of the tire 102, FIG. 12A. Positioned above the opening 106 in the conveyor and the tire is the detection unit 110 and a drive spindle 112.

Figure 12A:
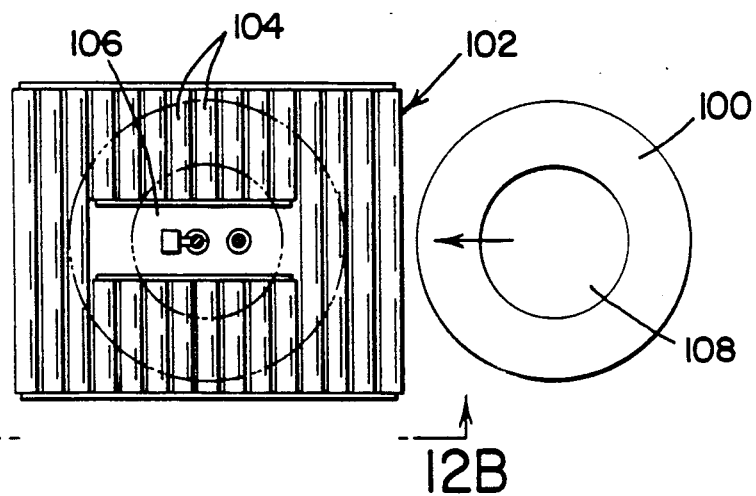
FIG. 12A-G are plan and elevational views according to the steps of Example 2.
Figure 12B:
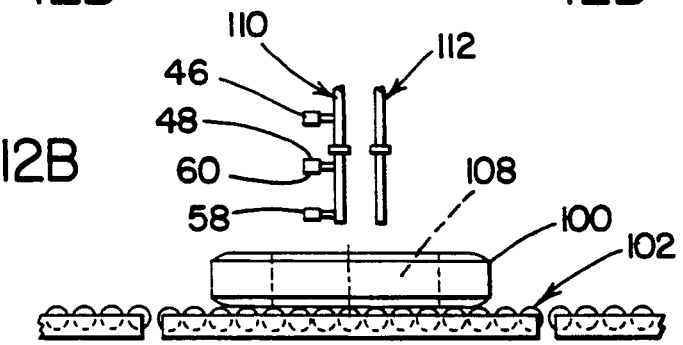
Figure 12C:
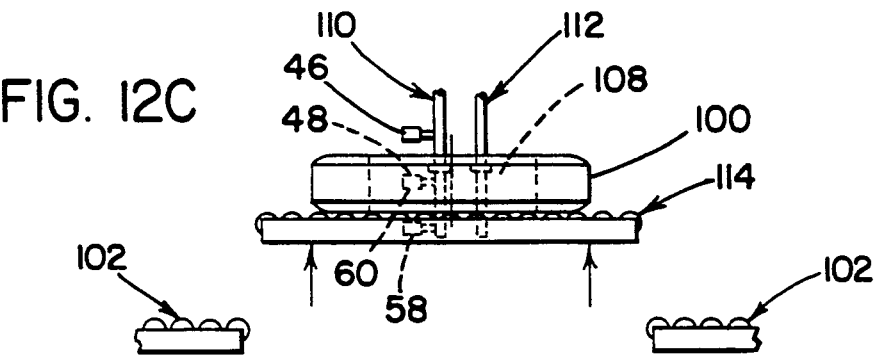

A section of the conveyor 114 is actuated to move upwardly with the tire to pass both the detection unit 110 and the drive spindle 112 within the opening 108 of the tire 100, FIG. 12C. More specifically the detection unit is positioned such that the radiation sources 46, 58 are located outside of the tire cavity while both sensors 48, 60 are located within the tire cavity.

Figure 12D:
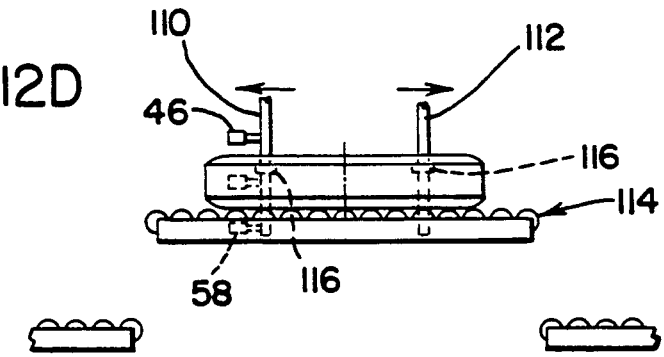
Figure 12E:
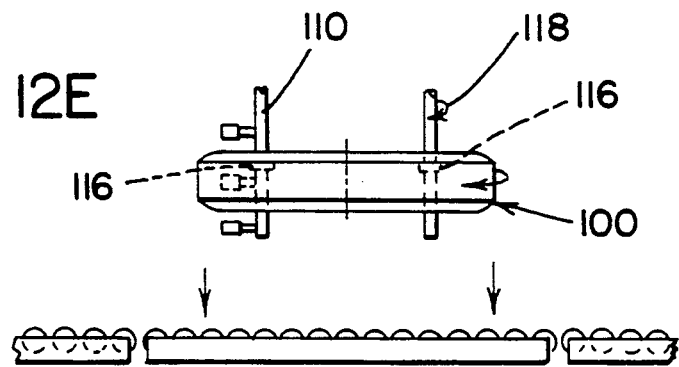
Figure 12F:
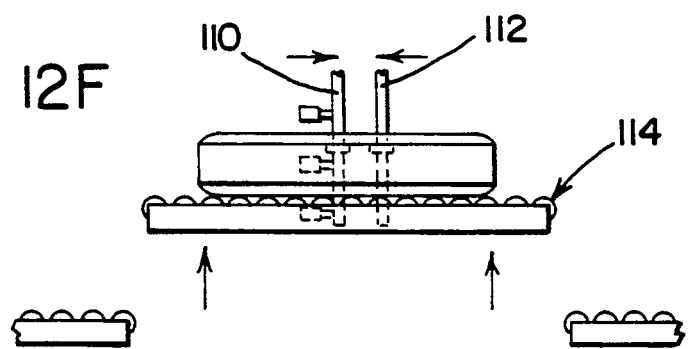
Figure 12G:
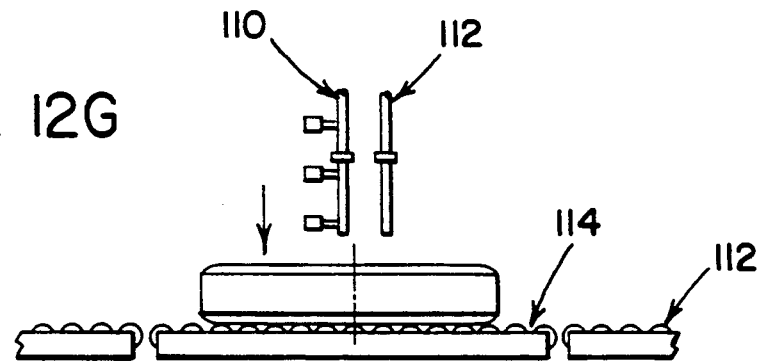

The detection unit 110 and the drive spindle 112 then move to engage the beads of the tire, FIG. 12D. In so doing, a sidewall of the tire is interposed between a combination of a radiation source and the associated sensor. Both the detection unit 110 and the drive spindle 112 are provided with a collar 116 which engages the bead of the tire. Once so engaged, the movable section 114 of the conveyor is retracted, FIG. 12C, and the tire is supported by the collars of the detection unit 110 and the drive spindle 112.

The drive spindle 112 is then actuated to begin rotation 118 which in turn rotates the tire. Once the tire has reached a stable predetermined speed, the detection unit scans the tire sidewalls. Upon completion of the scanning, the rotation of the drive spindle is stopped, and the movable section of the conveyor 114 is actuated to engage the tire 100, FIG. 12F. The drive spindle 112 and detection unit 110 are then actuated to disengage from the beads of the tire and are retracted to their original position. The movable section of conveyor 114 is then retracted with the tire.

Tires which fail the inspection can be marked in an appropriate manner and can either be removed from the line at this stage or at some other downstream point. It is also preferred that a failed tire will actuate an alarm. Tires which pass the inspection can then continue down the production line.

In that the detection unit must be inserted within the bead opening of a tire, it must have an overall width which will allow for such insertion in the type of tires to be tested.

These descriptions and details have been shown for the purpose of illustrating this invention and it will become apparent to those skilled in the art that various changes and/or modifications may be made therein without departing from the original spirit or scope of the invention.

It is claimed:

1. An apparatus for detecting missing or overlapping cords within an elastomer of the sidewalls of a tire, the apparatus comprising:
   (a) a radiation source or sources for providing a collimated beam of radiation through each tire sidewall, such radiation being less attenuated or reflected by the elastomer of said sidewalls than by the cords;
   (b) a sensor or sensors aligned in combination with said radiation source or sources, said sensor or sensors detecting said collimated radiation and, generating an electrical signal in response to said radiation;
   (c) a positioning arm, said radiation source or sources and said sensor or sensors being attached to said positioning arm;
   (d) means for moving and holding at tire in said apparatus while allowing it to be rotated in association with a positioning means for causing said positioning arm to interpose a tire sidewall between each radiation source and sensor
   (e) a means for causing said radiation source or sources and sensor to scan along a section of tire sidewall at a predetermined speed;
   (f) means responsive to said electrical signal generated by said sensor or sensors for a providing timing signal when said sensor bears a predetermined relationship to each scanned cord in the tire sidewall; and
   (g) means responsive to said timing signal associated with said sensor or sensors during a predetermined scan for measuring the time each scanned cord is between a radiation source and a sensor.

2. The apparatus of claim 1 wherein the means responsive to the electrical signal generated by said sensor or sensors provides a measure of when a scanned cord is not between a radiation source and a sensor.

3. The apparatus of claim 1 wherein said positioning arm comprises a first elongated member; and second, third, and fourth elongated members attached to and extending from said first member in spaced relationship to each other and in alignment with each other, said second member carrying said sensors and said third and fourth members carrying said first and second radiation sources, respectively.

4. The apparatus of claim 1 wherein the collimated beams of radiation are passed to the inner portion of the ire through the sidewalls.

5. The apparatus of claim 3 wherein said means for causing said radiation source and said sensor to scan comprises a means for rotating the tire with respect to the positioning arm.

6. The apparatus of claim 3 wherein said means or causing said radiation source and said sensor to scan comprises a means for rotating the positioning arm with respect to the tire.

7. A method of detecting defects in tire sidewalls, the method comprising the steps of:
  (a) interposing a tire sidewall between a radiation source or sources and a sensor or sensors diametrically opposed to a radiation source;
  (b) passing a collimated beam of radiation from a radiation source or sources through at tire sidewall, such radiation being less attenuated or reflected by the elastomer of the sidewall than by the cords;
  (c) detecting said radiation passing through a tire sidewall by a sensor or sensors;
  (d) causing each said radiation source and sensor to scan along a section of tire sidewall at a predetermined speed;
  (e) providing a timing signal, responsive to an electrical signal received by a sensor when said sensor bears a predetermined relationship to each scanned cord in the tire sidewall;
  (f) measuring the time each scanned cord is between a radiation source and a sensor, responsive to the respective timing signals generated, and
  (g) summing the total time the cords of a predetermined window of a scan are between a radiation source and sensor; and comparing said sum to a reference value.

8. The method of claim 7 wherein the collimated beams of radiation are passed from the exterior of the tire inwardly through the sidewall.

9. The method of claim 7 further comprising the steps of summing total time the cords of a predetermined window are between a radiation source and sensor; and comparing said sum to a reference value.

10. The method of claim 9 wherein said reference value is determined by taking the average of the summation of the total time cords of a window are between a source and sensor for a predetermined number of windows.

11. The method of claim 7 further comprising the steps of measuring the time a scanned cord is not between a radiation source and a sensor, responsive to the electrical signals generated by said sensor.

12. The method of claim 7 further comprising the steps of measuring a time interval beginning from the moment a scanned cord is between a radiation source and a sensor until the next adjacent scanned cord is between said radiation source and sensor, responsive to the electrical signals generated by said sensor.

13. The method of claim 10 further comprising the steps of measuring the time a scanned cord is not between a radiation source and a sensor, responsive to the electrical signals generated by said sensor.

14. The method of claim 10 further comprising the steps of measuring a time interval beginning from the moment a scanned cord is between a radiation source and sensor until the next adjacent scanned cord is between a radiation source and sensor, responsive to the electrical signals generated by said sensor.

15. An apparatus for detecting missing or overlapping cords within an elastomer of the sidewalls of at tire, the apparatus comprising:
  (a) a radiation source or sources for providing a collimated beam of radiation through each tire sidewall, such radiation being less attenuated or reflected by the elastomer of said sidewalls than by the cords;
  (b) a sensor or sensors aligned in combination with said radiation source or sources, said sensor or sensors detecting said collimated radiation and, generating an electrical signal in response to said radiation;
  (c) a positioning arm, said radiation source or sources and said sensor or sensors being attached to said positioning arm;
  (d) a positioning means for causing said positioning arm to interpose a tire sidewall between each radiation source and sensor wherein said positioning arm comprises a first elongated member; and second, third, and fourth elongated members attached to and extending from said first member in spaced relationship to each other and in alignment with each other, said second member carrying said sensors and said third and fourth members carrying a first radiation source and an optional second radiation source; respectively,
  (e) a means for causing said radiation source or sources and sensor to scan along a section of tire sidewall at a predetermined speed;
  (f) means responsive to said electrical signal generated by said sensor or sensors for a providing timing signal when said sensor bears a predetermined relationship to each scanned cord in the tire sidewall; and
  (g) means responsive to said timing signal associated with said sensor to sensors during a predetermined scan for measuring the time each scanned cord is between a radiation source and a sensor.

* * * * *